United States Patent [19]

Bohn et al.

[11] Patent Number: 4,957,730
[45] Date of Patent: Sep. 18, 1990

[54] ANTIMYCOTIC NAIL VARNISH

[75] Inventors: Manfred Bohn; Walter Dittmar, both of Hofheim am Taunus; Heinz G. Peil, Bad Nauheim; Eberhard Futterer, Kelkheim; Karl Kraemer, Langen, all of Fed. Rep. of Germany

[73] Assignee: Hoechst Aktiengesellschaft, Frankfurt am Main, Fed. Rep. of Germany

[21] Appl. No.: 942,699

[22] Filed: Dec. 17, 1986

[30] Foreign Application Priority Data

Dec. 19, 1985 [DE] Fed. Rep. of Germany ....... 3544983

[51] Int. Cl.⁵ .............................................. A61K 7/043
[52] U.S. Cl. ...................................... 424/61; 514/345; 546/290
[58] Field of Search ........................... 424/61; 546/290; 514/345

[56] References Cited

U.S. PATENT DOCUMENTS

| 2,752,356 | 6/1956 | Cislak | 260/297 |
| 3,269,904 | 8/1966 | Bernstein et al. | 167/58 |
| 3,883,545 | 5/1975 | Lohaus et al. | 546/290 |
| 3,968,118 | 7/1976 | Lohaus et al. | 260/297 Z |
| 4,185,106 | 1/1980 | Dittmar et al. | 424/263 |
| 4,250,164 | 2/1981 | Bernstein | 424/61 |

FOREIGN PATENT DOCUMENTS

| 1175355 | 10/1984 | Canada . |
| 0055397 | 8/1984 | European Pat. Off. . |
| 0140325 | 5/1985 | European Pat. Off. . |
| 1795831 | 5/1976 | Fed. Rep. of Germany . |
| 3140054 | 5/1983 | Fed. Rep. of Germany . |
| 87/02580 | 5/1987 | PCT Int'l Appl. . |

OTHER PUBLICATIONS

Dittmar et al., C.A., 92:47183b, Feb. 1980, No. 6.
Lohaus et al., Arzneimittel Forschung (Drug Research) 31, (II) 1981, pp. 1311-1316.
Fungiplex Nail Varnish, Prospectus of Hermal-Chemie Kurt Herrmann, Hamburg, Fed. Rep. of Germany.
O. Male, Therapie der Pilzkrankheiten, WMW Sonderheft 1/1983, pp. 27-34.
Aldrich, p. 860 (1988).
Kellner et al, Chem. Abstracts, 95, 225547v, (1981).

Primary Examiner—John W. Rollins
Assistant Examiner—W. Catchpole
Attorney, Agent, or Firm—Finnegan, Henderson, Farabow, Garrett, and Dunner

[57] ABSTRACT

A nail varnish comprising a water-insoluble film-forming substance and an antimycotic compound which is a 1-hydroxy-2-pyridone I of the general formula

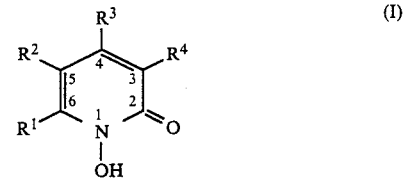

in which $R^1$ is a hydrocarbon group which contains from 6 to 9 carbon atoms, but is free from olefinic and acetylenic bonds, one of the groups $R^2$ and $R^4$ is hydrogen and the other is hydrogen, methyl or ethyl and $R^3$ is alkyl having up to two carbon atoms, said antimycotic ingredient being present in free form or in the form of a salt.

21 Claims, No Drawings

ANTIMYCOTIC NAIL VARNISH

Fungal diseases of the nails (onychomycoses) are persistent disease forms which it has as yet not been possible to treat satisfactorily. The term onychomycoses summarize various types of nail mycoses, of which those caused by dermatophytes are most difficult to treat, whilst those nail mycoses caused by yeast fungi have hitherto been the most likely to be successfully treated.

The problem with onychomycoses caused by dermatophytes is also that they make a considerable contribution to the spread of infectious fungi. Various avenues have so far been explored to treat them, but without impressive success.

One treatment method, the systemic method, consisted of oral administration of fungus-inhibiting agents. This required long-term treatment, which experience shows can lead to intoxication.

Another method consists in removing the nail surgically or by the action of chemicals and hoping that healthy unaffected nails subsequently grow. This method is of course very aggressive and also gives no guarantee that the nails subsequently grow in the natural form; rather, the nails which subsequently grow are frequently misshapen.

A third but gentler method consists in treating the nails locally with specific antimycotic substances. The most diverse treatment methods have been attempted here. Thus, in a combined treatment, the nails have first been treated with solutions of the antimycotic substances and in each case cream dressings have been applied at night. This treatment method is also of course very unpleasant and mentally disturbing to the patient. On the one hand, it is necessary to treat the nails with solutions several times a day. On the other hand, they must be covered with dressings, especially at night. Furthermore, continuous filing of the diseased nails is necessary, which is both tiresome and also contributes to spreading of the pathogens. This all means that the treatment, which usually lasts many months, is frequently not endured by the patient, but rather discourages the patient and makes him negligent, so that the therapy is unsuccessful. The success of the treatment with this method is furthermore impaired by the fact that the solutions and creams are usually water-miscible or hydrophilic and can therefore be removed again from the nail surface or dissolved out of the nail during washing, bathing and showering, and consequently must be subsequently applied again.

Great hopes have therefore been placed in a completely different method, that is to say in treatment with a nail varnish which contains the antimycotic substance sulben tine, a thiadiazine compound. Although this method has already been practiced for about twenty years, it has not found general acceptance in therapy, since almost exclusively milder nail mycoses can be combated with these nail varnishes. This formulation probably also failed to achieve satisfactory success due to a lack of sufficient bioavailability of the active compound from the solid system present after the varnish dries.

Many cases, in particular the more severe, have therefore continued to be treated with the surgical or chemical methods described above or with the combined solution and cream therapy.

It has now been found that nail mycoses can be treated with impressive success or the attack can be prevented if the nail varnish according to the invention is applied to the nails, in particular to the diseased nails.

The invention relates to a nail varnish against nail mycoses containing a water-insoluble film-forming agent and an antimycotic substance, which contains 1-hydroxy-2-pyridones of the general formula I (see claim 1), in which $R^1$ denotes a "saturated" hydrocarbon radical with 6 to 9, preferably 6 to 8, carbon atoms, one of the radicals $R^2$ and $R^4$ denotes a hydrogen atom and the other denotes hydrogen, methyl or ethyl and $R^3$ denotes an alkyl radical with one or two carbon atoms, as the active compound, it being possible for these active compounds to be present either in the free form or in the form of their salts. The term "saturated" here designates those radicals which contain no aliphatic multiple bonds, that is to say no ethylenic or acetylenic bonds.

A radical cure can be achieved in the treatment of nail mycoses with the nail varnish according to the invention, the nail usually subsequently growing without deformation. In view of the previous poor experiences of therapy, this is an extremely important finding.

The nail varnish according to the invention is also suitable for prophylactic use against nail mycoses, a sufficiently high depot of active compound in the nail being achieved, so that in the event of fungal contamination, a nail disease caused by fungi cannot break out.

The content of active compound in the nail varnish according to the invention depends on the structure of each active compound and hence on the release thereof from the film of varnish, its penetration properties in the nail and its antimicrobial properties.

The nail varnish according to the invention, that is to say the use form containing solvents, in general contains the active compound in an amount of 0.5 to 20, preferably 2 to 15, percent by weight. The minimum content of active compound in the medicinal nail varnishes, that is to say those for treatment, is usually 4 percent by weight; the nail varnishes used for prophylaxis usually contain less than 4 and advantageously at least 1 percent by weight of active compound. The nail varnishes according to the invention in general contain the active compound in an amount of 2 to 80, preferably 10 to 60 and in particular 20 to 40 percent by weight, in each case based on the amount of non-volatile constituents, that is to say the sum of film-forming agents, any pigments and plasticizers present and other non-volatile additives as well as the active compound.

In the formula I, the hydrocarbon radical $R^1$ is an alkyl or cyclohexyl radical which can also be bonded to the pyridone ring by a methylene or ethylene group or can contain an endomethylene group. $R^1$ can also represent or contain an aromatic radical, but this is preferably bonded to the pyridone radical by at least one aliphatic C atom.

Examples which may be mentioned of suitable active compounds are 1-hydroxy-4-methyl-6-n-hexyl, -6-iso-hexyl-, -6-n-heptyl- or -6-iso-heptyl-2-pyridone, 1-hydroxy-4-methyl-6-octyl- or -6-iso-octyl-2-pyridone, in particular as 1-hydroxy-4-methyl-6-(2,4,4-trimethylpentyl)-2-pyridone, 1-hydroxy-4-methyl-6-cyclohexyl-2-pyridone, 1-hydroxy-4-methyl-6-cyclohexylmethyl- or -6-cyclohexyl-ethyl-2-pyridone, it being possible for the cyclohexyl radical in each case to carry a further methyl radical, 1-hydroxy-4-methyl-6-(2-bicyclo[2,2,1]heptyl)-2-pyridone, 1-hydroxy-3,4-dimethyl-6-benzylor -6-dimethylbenzyl-2-pyridone and 1-hydroxy-4-methyl-6-(8-phenyl-ethyl)-2-pyridone.

The nail varnishes according to the invention also contain, as necessary constituents and in addition to the active compound dissolved in a solvent or solvent mixture, one or more film-forming agents which form a water-insoluble film on the nail after the formulation has dried.

Examples of suitable film-forming agents are substances based on cellulose nitrate or physiologically acceptable polymers, such as are customary, for example, in cosmetics, preferably as a mixture with cellulose nitrate. Examples which may be mentioned are polyvinyl acetate and partially hydrolyzed polyvinyl acetate, copolymers of vinyl acetate on the one hand and acrylic acid or crotonic acid or maleic acid monoalkyl esters on the other hand, ternary copolymers of vinyl acetate on the one hand and crotonic acid and vinyl neodecanoate, or crotonic acid and vinyl propionate on the other hand, copolymers of methyl vinyl ether and maleic acid monoalkyl esters, in particular as maleic acid monobutyl ester, copolymers of fatty acid vinyl esters and acrylic acid or methacrylic acid, copolymers of N-vinyl pyrrolidone, methacrylic acid and methacrylic acid alkyl esters, copolymers of acrylic acid and methacrylic acid or acrylic acid alkyl esters or methacrylic acid alkyl esters, polyvinyl acetals and polyvinyl butyrals, alkyl-substituted poly-N-vinylpyrrolidones, alkyl esters of copolymers of olefins and maleic anhydride and reaction products of colophony with acrylic acid. The alkyl radicals in the esters are usually short-chain and usually have not more than 4 carbon atoms.

Possible physiologically acceptable solvents are substances such as the hydrocarbons, halogenated hydrocarbons, alcohols, ethers, ketones and esters customary in cosmetics, in particular acetic acid esters of monohydric alcohols, such as ethyl and butyl acetate, if appropriate mixed with aromatic hydrocarbons, such as toluene and/or alcohols, such as ethanol or isopropanol.

As is known, the combination of the solvents is of decisive importance for the drying time, brushability and other important properties of the varnish or varnish film. The solvent system preferably consists of an optimum mixture of low-boiling constituents (=solvents with a boiling point up to 100° C.) and medium-boiling constituents (=solvents with a boiling point up to 150° C.), if appropriate with a small amount of high-boiling constituents (=solvents with a boiling point up to 200° C.).

The nail varnishes according to the invention can furthermore contain the additives customary in cosmetics, such as plasticizers based on phthalate or camphor, dyestuffs or colored pigments, nacreous agents, sedimentation retarders, sulfonamide resins, silicates, aroma substances, wetting agents, such sodium dioctyl sulfosuccinate, lanolin derivatives, light stabilizers, such as 2-hydroxy-4-methoxybenzophenone, antibacterial substances and substances with a keratolytic and/or keratoplastic action, such as ammonium sulfite, esters and salts of thioglycolic acid, urea, allantoin, enzymes and salicylic acid.

Colored or pigmented nail varnishes have the advantage, for example, that the formulation according to the invention can be adapted to suit the cosmetic sense of the patient.

The nail varnish is prepared in the customary manner by bringing the individual components together and—if necessary—subjecting them to further processing suitable for the particular formulation.

The nail varnishes according to the invention also differ in principle from the antimycotic agents known from European Patent No. 55,397, which contain azole derivatives, in particular imidazole derivatives and triazole derivatives, as active compounds. These antimycotic agents are said to be applied as a water-soluble film, have a depot action and permit short-term therapy. They are also said to be suitable for the treatment of nail mycoses and to be used both in solutions and in sprays which form a water-soluble film after drying. The use of such water-soluble binders has the effect of course that the agent applied is removed to a greater or lesser degree each time the nails are washed.

The use of water-insoluble film-forming polymers according to the present invention is in stark contrast to the information in European Patent No. 55,397, according to which, if water-insoluble polymers, for example "methacrylates", are used instead of the formulations containing water-soluble polymers described therein, the mycosis is worsened.

In contrast, nail mycosis can be successfully treated with the aid of the nail varnishes according to the invention which contain film-forming polymers which become water-insoluble after drying.

As is known, the upper horny layers have the biological task, inter alia, of warding off penetrating foreign substances. The formulations according to the invention also differ, and do so in a fundamental manner, from the formulations previously recommended for nail treatment in that they contain those active compounds which are admitted to a considerable degree by the upper horny layers and thus exert a long-lasting action in the deeper layers. Penetration of the horny layers in an effective concentration is accordingly a peculiarity of the pyridone compounds used according to the invention which is to be separated from the antimycotic property and which, for the first time, allows nail mycoses to be treated in a simple and effective manner.

The action of the compounds used according to the invention has been demonstrated in penetration tests on excised horny skin and in clinical treatment trials on patients with onychomycoses. The test method for penetration capacity on excised skin from pigs enables the capacity to penetrate of an effective concentration of compounds horny tissue to be tested.

The present invention is illustrated in more detail by the following examples. The percentage amounts given are based on the weight. P denotes parts by weight.

EXAMPLES 1-8—TESTING OF THE EFFICACY

In the tests for the penetration capacity, the surface of shaved pieces of skin was first treated with 0.3% strength solutions of the compounds 1-8 and likewise with three similar compounds not claimed, in each case dissolved in a mixture of 1 ml of dimethyl sulfoxide and 9 ml of isopropanol, at room temperature and was washed again after 2 hours. The lowest region of the horny layer was then exposed by removing the superficial layers by peeling off with adhesive strips ten times in succession. The deep-lying horny layer now exposed was inoculated with virulent pathogens of nail mycoses (dermatophytes). Conclusions as to the level of the penetration capacity were drawn on the basis of the degree of growth inhibition found.

The results of these experiments are shown in Table 1 in comparison with the efficacy of the pyridone compounds against the highly virulent skin fungus Trichophyton mentagrophytes 109 (100/25) in the in vitro series dilution test and in the guinea pig trichophytosis model.

Although the compounds 1-8 showed similar results to comparison compounds 1-3 in the testing for antimycetic efficacy in the series dilution test and for antimycotic action in the guinea pig trichophytosis model on superficial horny layers, the growth inhibition in the lowest region of the horny layer of pig skin shows that compounds 1-8 have a considerably better penetration capacity than comparison compounds 1-3.

EXAMPLES 9 and 10—TESTING OF THE EFFICACY WITH A NAIL VARNISHES

In further experiments, the substantially thicker horny human skin was treated by the test method described above at room temperature for 1 or 2 hours with 3% strength nail varnishes of compounds 9 and 10 and likewise with a similar compound 4, which is not claimed, in comparison with the abovementioned nail varnish containing sulbentine. The varnish base of examples 9 and 10 and of comparison 4 and 5 was prepared by mixing the following constituents:
Isopropyl alcohol: 34.4%
Ethyl acetate: 34.5%
2-Hydroxy-4-methoxybenzophenone: 0.1%
Sodium dioctyl sulfosuccinate: 1.0%
50% strength solution of a copolymer of methyl vinyl ether and monobutyl maleate in isopropyl alcohol: 30.0%

The results of the experiments with varnish formulations on human skin shown in Table 2 are in good agreement with the results of the studies carried out with active compound solutions on pig skin. Whilst the varnishes which contain compounds 9 and 10 almost completely or completely inhibit the growth of Trichophyton mentagrophytes in the d lying horny layer of human skin, the varnishes containing comparison compound 4—like the varnish containing sulbentine—have only an inadequate inhibiting effect.

EXAMPLES 11-14

Some compounds according to the invention are processed to give nail varnishes as follows (examples 11-13 colorless, example 14 pigmented). The colorless nail varnishes are prepared by dissolving the various components in the solvents.
11. Isopropyl alcohol: 57.5%
Ethyl acetate: 33.0%
Polyvinyl butyral: 3.8%
Cellulose nitrate: 3.1%
Dibutyl phthalate: 0.6%
1-Hydroxy-4-methyl-6-(2,4,4-trimethylpentyl)-2-pyridone: 2.0%
12. Isopropyl alcohol: 27.0%
Ethyl acetate: 27.0%
50% solution of a copolymer of methyl vinyl ether and monobutyl maleate in isopropyl alcohol: 34.0%
1-Hydroxy-4-methyl-6-cyclohexyl-2-pyridone: 12.0%
13. Ethanol: 5.0%
Ethyl acetate: 68.5%
Methyl acetate: 10.0%
Polyvinyl acetate (for example Mowilith ®30): 12.5%
1-Hydroxy-4-methyl-6-cyclohexyl-2-pyridone: 4.0%
14. A thixotropic paste was prepared by slowly stirring 10 P of an organically modified montmorillonite (for example Bentone 27 ®, Kronos Titan GmbH, Leverkusen, Germany) into 80 P of toluene and subsequently adding 8 P of wetting agent (for example Anti-Terra-U ®, Byk-Mallinckrodt, Wesel, Germany) and 2 P of methanol. A clear varnish was also prepared by dissolving 22 P of butanol-moist collodion cotton (for example type E 510, Wolff Walsrode AG, Germany) and 8 P of toluene sulfonamide resin (for example Santolite MS 80 ®, Monsanto, Mulheim-Ruhr, Germany) in a mixture of 3 P of dibutyl phthalate, 20 P of ethyl acetate, 10 P of butyl acetate, 7 P of ethyl alcohol and 30 P of toluene. 40 P of DC ROT No. 7 calcium varnish (for example color pigment C 19021, Sun Chemical Corporation, Pigments Division, Fort Lee, U.S.A.) and 60 P of dibutyl phthalate were also processed to give a color paste with a particle size of less than 1 μm.

To prepare the pigmented nail varnish, 12 P of thixotropic paste and 0.8 P of anti-settling agent (for example MPA 2000 X ®, Kronos Titan GmbH) were dispersed in 83.7 P of clear varnish, during which operation a temperature of at least 38° C. was to be reached. 1 P of 1-hydroxy-4-methyl-6-(2,4,4-trimethylpentyl)-2-pyridone was then dissolved in the thixotropic clear varnish and 2.5 P of color paste was stirred in. The finished nail varnish was filtered through a 70 μm sieve.

TABLE 1

| | Formula I according to Patent claim 1 | | | | Action against T. mentagrophytes | | |
|---|---|---|---|---|---|---|---|
| | | | | | in vitro* | in vivo** Inhibition | in vitro*** Inhibition (%) in the horny |
| | $R^1$ | $R^2$ | $R^3$ | $R^4$ | MIC (μg/ml) | (%) on skin | layer |
| Example | | | | | | | |
| 1 | n-$C_7H_{15}$ | H | $CH_3$ | H | 1,95 | 89,4 | 97,0 |
| 2 | $C_4H_9$\\ CH— /$C_2H_5$ | H | $CH_3$ | H | 1,95 | 85,6 | 85,8 |
| 3 | 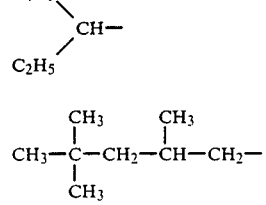 | H | $CH_3$ | H | 1,95 | 91,9 | 99,6 |

TABLE 1-continued

| | Formula I according to Patent claim 1 | | | | Action against *T. mentagrophytes* | | |
|---|---|---|---|---|---|---|---|
| | R¹ | R² | R³ | R⁴ | in vitro* MIC (μg/ml) | in vivo** Inhibition (%) on skin | in vitro*** Inhibition (%) in the horny layer |
| 4 | cyclohexyl (–C₆H₁₁) | H | CH₃ | H | 1,95 | 88,0 | 98,0 |
| 5 | –CH₂–CH₂–cyclohexyl | H | CH₃ | H | 1,95 | 88,0 | 81,2 |
| 6 | norbornyl | H | CH₃ | H | 1,95 | 88,0 | 79,9 |
| 7 | –CH₂–(2,4-dimethylphenyl) (mesityl-CH₂) | H | CH₃ | CH₃ | 1,95 | 88,8 | 80,0 |
| 8 | –CH₂–CH₂–phenyl | H | CH₃ | H | 1,95 | 88,0 | 81,9 |
| Comparison | | | | | | | |
| 1 | –CH(CH₃)₂ | H | CH₃ | H | 1,95 | 75,0 | 35,7 |
| 2 | –C₁₁H₂₃ | H | CH₃ | H | 3,90 | 100,0 | 9,8 |
| 3 | –(CH₂)₄–phenyl | H | CH₃ | H | 3,90 | 88,0 | 24,2 |

*Minimum inhibitory concentration (MIC) in the series dilution test
**Percentage inhibition on the skin surface in the guinea pig Trichophytosis model (W. Dittmar, Mykosen 18 (8), 351-361 (1975))
***Horny layer penetration: percentage growth inhibition by the substance which has penetrated into the lowest part of the horny layer.

TABLE 2

| | Formula I according to patent claim 1 | | | | Action against *T. metagrophytes* Inhibition (%) in the deep horny layer | | |
|---|---|---|---|---|---|---|---|
| | | | | | Pig (0.3% strength solutions) | Humans (3% strength varnishes) | |
| | R¹ | R² | R³ | R⁴ | Action time* (min) | | |
| | | | | | 120 | 60 | 120 |
| Example | | | | | | | |
| 9 | CH₃–C(CH₃)₂–CH₂–CH(CH₃)–CH₂– | H | CH₃ | H | 99,6 | 99,0 | 99,9 |
| 10 | cyclohexyl | H | CH₃ | H | 98,0 | 100,0 | 100,0 |
| Comparison | | | | | | | |
| 4 | –C₁₁H₂₃ | H | CH₃ | H | 9,8 | 51,4 | 49,4 |
| 5 | blank varnish | | | | — | 1,0 | 0,0 |
| 6 | untreated | | | | 0,0 | 0,0 | 0,0 |
| 7 | nail varnish containing sulbentine | | | | — | 30,0 | 22,4 |

*Time between application of the product and stripping of the skin

We claim:

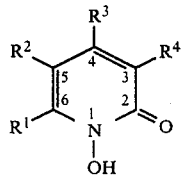 (I)

in which $R^1$ is a hydrocarbon group which contains from 6 to 9 carbon atoms, but said hydrocarbon group being free from olefinic and acetylenic bonds, one of the groups $R^2$ and $R^4$ is hydrogen and the other is hydrogen, methyl or ethyl and $R^3$ is alkyl having up to two carbon atoms, said antimycotic ingredient being present in free form or in the form of a salt, and in an amount effective against nail mycoses.

2. A nail varnish according to claim 1, wherein in compound I $R^2$ and $R^4$ are hydrogen.

3. A nail varnish according to claim 1, wherein the compound I $R^1$ contains a cyclic group.

4. A nail varnish according to claim 3, wherein the group is a cyclohexyl group.

5. A nail varnish according to claim 1, wherein $R^1$ is a cyclohexyl group.

6. A nail varnish according to claim 2, wherein in compound I $R^1$ contains a cyclic group.

7. A nail varnish according to claim 6, wherein the cyclic group is a cyclohexyl group.

8. A nail varnish according to claim 1, wherein $R^1$ is a cyclohexyl group and $R^2$ and $R^3$ are hydrogen.

9. A nail varnish according to claim 1, wherein in compound I $R^1$ is an octyl group.

10. A nail varnish according to claim 2, wherein in compound I $R^1$ is an octyl group.

11. A nail varnish according to claim 9, wherein the octyl group has the formula —$CH_2$—$CH(CH_3)$—$CH_2$—$C(CH_3)_3$.

12. A nail varnish according to claim 10, wherein the octyl group has the formula —$CH_2$—$CH(CH_3)$—$CH_2$—$C(CH_3)_3$.

13. A nail varnish according to claim 1, wherein compound I is contained in an amount of from 2 to 80% by weight, based on the amount of the non-volatile components.

14. A nail varnish according to claim 1, wherein compound I is contained in an amount of from 10 to 60% by weight, based of the amount of the non-volatile components.

15. A nail varnish according to claim 1, wherein compound I is contained in an amount of from 20 to 40% by weight, based on the amount of the non-volatile components.

16. A nail varnish according to claim 1, wherein compound I is contained in an amount of from 0.5 to 20% by weight.

17. A nail varnish according to claim 1, wherein compound I is contained in an amount of from 2 to 15% by weight.

18. A nail varnish according to claim 16, which is a medicated nail varnish and contains compound I in an amount of at least 4% by weight.

19. A nail varnish according to claim 16, wherein compound I is contained in an amount of less than 4% by weight.

20. A nail varnish according to claim 16, wherein compound I is contained in an amount of at least 1% by weight.

21. A method of treating onychromycosis which comprises applying to a nail infested by onchomycosis a nail varnish as defined in claim 1 and containing an effective amount of compound I.

* * * * *

UNITED STATES PATENT AND TRADEMARK OFFICE
CERTIFICATE OF CORRECTION

PATENT NO. : 4,957,730
DATED : September 18, 1990
INVENTOR(S) : Manfred Bohn et al.

It is certified that error appears in the above-identified patent and that said Letters Patent is hereby corrected as shown below:

Claim 1, Column 9, Line 1, the formula should be preceded by --1. A nail varnish comprising a water insoluble film-forming substance and an antimycotic compound which is a 1-hyroxy-2-pyridone of the formula(I)--;

Claim 3, Column 9, Line 21, "the" should be --in--;

Claim 4, Column 9, Line 25, "group" (first occurrence) should be preceded by --cyclic--.

Signed and Sealed this

First Day of September, 1992

Attest:

DOUGLAS B. COMER

*Attesting Officer*   *Acting Commissioner of Patents and Trademarks*